US009329054B2

(12) United States Patent
Crook et al.

(10) Patent No.: US 9,329,054 B2
(45) Date of Patent: May 3, 2016

(54) ADJUSTMENT OF MEASUREMENT SYSTEM COMPONENTS

(75) Inventors: David T. Crook, Loveland, CO (US); Areef A. Moin, Fort Collins, CO (US)

(73) Assignee: Hach Company, Loveland, CO (US)

( * ) Notice: Subject to any disclaimer, the term of this patent is extended or adjusted under 35 U.S.C. 154(b) by 292 days.

(21) Appl. No.: 13/432,939

(22) Filed: Mar. 28, 2012

(65) Prior Publication Data

US 2013/0256515 A1    Oct. 3, 2013

(51) Int. Cl.
*G01D 3/02* (2006.01)
*G01N 21/64* (2006.01)

(52) U.S. Cl.
CPC .............. *G01D 3/022* (2013.01); *G01N 21/643* (2013.01); *G01N 2021/6432* (2013.01)

(58) Field of Classification Search
CPC ................... G01N 21/643; G01N 2021/6432; G01J 1/42; G01D 3/022
USPC ................. 250/208.1, 216, 221, 222.1, 239, 250/573–577, 214 R; 356/39, 40, 301; 600/345, 347
See application file for complete search history.

(56) References Cited

U.S. PATENT DOCUMENTS 6,798,347 B2 * 9/2004 Henry et al. .................. 340/680
8,173,438 B1 * 5/2012 Putnam et al. ................ 436/138
8,406,865 B2 * 3/2013 McKenna ..................... 600/547
2008/0088467 A1 * 4/2008 Al-Ali ........................... 340/679
2011/0077489 A1   3/2011 Say et al.

FOREIGN PATENT DOCUMENTS

DE        10218606 A1    11/2003
EP         2280249 A2     2/2011

OTHER PUBLICATIONS

European Patent Office, European Search Report for Application EP 13 16 0946, Jan. 27, 2016, 5 pages, European Patent Office, Munich, Germany.

* cited by examiner

*Primary Examiner* — Francis M Legasse, Jr.
*Assistant Examiner* — Don Williams
(74) *Attorney, Agent, or Firm* — Ference & Associates LLC

(57) ABSTRACT

One aspect provides a system including a sensor adjustment component comprising: a memory device having adjustment information stored therein; signal source capable of producing a signal detectable by a sensor to be adjusted; and one or more processors; wherein the one or more processors are configured to execute program instructions to operate the signal source to produce a predetermined signal pattern detectable by a measurement component of the sensor to be adjusted; and wherein the predetermined signal pattern comprises the adjustment information. Other aspects are disclosed.

20 Claims, 5 Drawing Sheets

ADJUSTMENT OF MEASUREMENT SYSTEM COMPONENTS

BACKGROUND

The subject matter described herein deals with measurement system component adjustment. Measurements systems in the context of this document include a component for obtaining measurements (referred to herein as a "sensor" or "probe"), where the component for obtaining measurements includes a replaceable sub-component or module (referred to throughout as a "sensor cap"), and a control component operatively connected to the component for obtaining measurements. The measurement system components may be provided as physically separate units or devices, or these units/devices may be integrated into a single unit that provides the appropriate functionality, as further described herein.

The sensor of a measurement system measures/monitors for various qualities in a given setting. A sensor may be sealed, such as for use in an aqueous environment, and measure/monitor characteristic(s) that may then be reported to a connected device (either a control component or other connected device(s)). For example, a luminescent dissolved oxygen (LDO) sensor is an optical sensor/probe that may be used to measure dissolved oxygen levels in an aqueous sample. An example of a dissolved oxygen sensor is the Advanced Hach LDO Process Dissolved Oxygen Probe, which is configured to continuously monitor dissolved oxygen in an aqueous sample using luminescent technology.

LDO sensors may be utilized for optical measurement of oxygen in several industrial applications, including but not limited to monitoring aquatic biology in waste water, blood gas analysis, fermentation control in biotechnology processes, wine microoxygenation, waste-water oxygen analysis, and industrial water applications. Optical measurement started with the measurement of relatively high oxygen levels, however now accurate measurement at levels below 1 $\mu g \cdot kg^{-1}$ are possible.

Operationally, LDO sensors may use a sensor cap portion that is coated with a luminescent material. The luminescent properties of the sensor cap are dependent on oxygen levels, forming the basis of operation. For example, in one example sensor, blue light from an LED illuminates a luminescent chemical in the luminescent material on the surface of the sensor cap. The luminescent chemical excites and then relaxes, releasing red light. The red light may be detected by a photodiode, with the time taken for the chemical to return to a relaxed state being measured. The red light that is given off by chemical is inversely proportional to the oxygen level of the sample. Thus, in higher oxygen environments, it takes a shorter amount of time for the luminescent material to return to a relaxed state. The oxygen concentration is thus inversely proportional to the time it takes for the luminescent material to return to a relaxed state.

BRIEF SUMMARY

In summary, one aspect provides a system, comprising: a sensor adjustment component comprising: a memory device having adjustment information stored therein; signal source capable of producing a signal detectable by a sensor to be adjusted; and one or more processors; wherein the one or more processors are configured to execute program instructions to operate the signal source to produce a predetermined signal pattern detectable by a measurement component of the sensor to be adjusted; and wherein the predetermined signal pattern comprises the adjustment information.

Another aspect provides a method comprising: providing adjustment information to a memory device of an adjustment component; and operating one or more processors configured to execute program instructions to operate a signal source of the adjustment component to produce a predetermined signal pattern detectable by a measurement component of a sensor to be adjusted; wherein the predetermined signal pattern comprises the adjustment information for adjusting the sensor to be adjusted.

A further aspect provides a system, comprising: an optical sensor adjustment component comprising: a memory device having a adjustment code stored therein; a light source capable of producing a light signal detectable by an optical sensor to be adjusted; and one or more processors; wherein the one or more processors are configured to execute program instructions to operate the light source to produce a predetermined light pattern detectable by a measurement component of the optical sensor to be adjusted; and wherein the predetermined light pattern comprises the adjustment information.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings.

DETAILED DESCRIPTION

Figure 1:
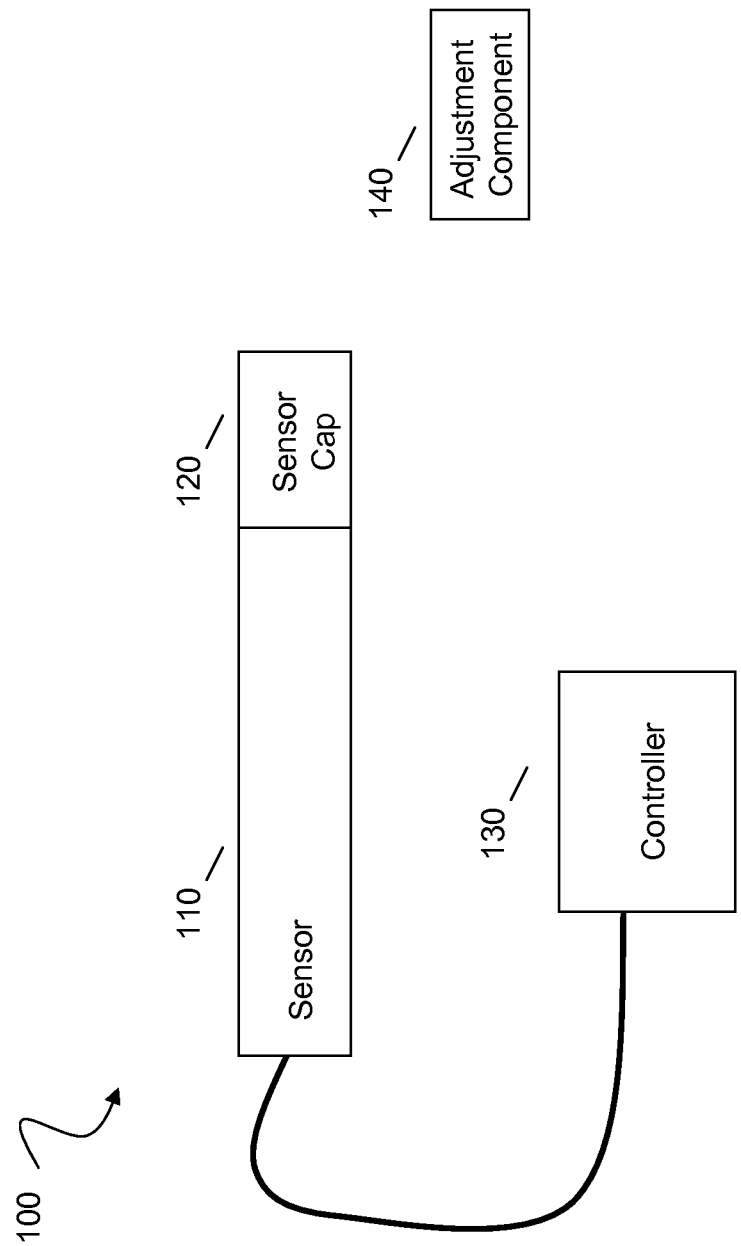
FIG. 1 illustrates an example adjustment component.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail to avoid obfuscation. The following description is intended only by way of example, and simply illustrates certain example embodiments.

Measurement system components require maintenance at different points in time. For example, when a sensor cap is replaced, the sensor/probe unit is paired with a new sensor cap sub-component, often from a different lot. Because of differences introduced in manufacturing sensor caps across lots, inherently each sensor cap lot produced has unique characteristics. Thus, sensor cap adjustment is necessary if consistent measurements are to be obtained when a sensor/probe has its sensor cap replaced.

At the factory, each lot of sensor caps is evaluated to determine an appropriate adjustment for a given lot. An adjustment algorithm may be utilized to define how to adjust the measurements of any given lot of sensor caps, such that a sensor that has its sensor cap replaced using a sensor cap from a different lot continues to give appropriate measurements. Thus, sensor caps from a lot may be evaluated such that the measurement system, for example the sensor/probe itself and/or a control component thereof, can be modified or adjusted to permit consistent measurements across sensor cap lots.

Conventionally, as part of this adjustment process, in some implementations each sensor cap from a lot may include a code (such as a printed number) that contains values used to populate variables in an adjustment function, for example, input via an attached controller. The code thus contains adjustment information specific for each lot of sensor caps as empirically determined at the factory using a complex calibration or normalization process, with the code providing the lot-specific variable information. When a replacement sensor cap was applied to an LDO sensor, in some implementations, a user manually entered the code into the controller attached to the sensor such that the sensor would be adjusted to make appropriate measurements when the sensor is paired with the new sensor cap.

Thus, when adjustment is required, such as when replacing a sensor cap for an LDO sensor, the user has in some implementations been required to enter a code into the controller, whereby the sensor is adjusted for use with a given replacement sensor cap. Among other difficulties, this required the user to manually enter the adjustment information, opening up the possibility for errant entry, and burdening the user with the manual entry. Moreover, in sealed sensors, such as those used in aqueous applications, a more convenient adjustment method is desirable.

Accordingly, an embodiment provides for convenient adjustment of measurement systems. An embodiment provides an adjustment component that transmits adjustment information without requiring manual entry of the adjustment information. An embodiment provides for adjustment of even sealed sensors by providing adjustment information via a measurement channel of the sensor, such that the sensor's sensing/measuring capabilities are utilized as a communication path for adjusting, thus imparting needed adjustment information via a channel already available to the sensor.

The description now turns to the figures. The example embodiments will be best understood by reference to the figures. The following description is intended only by way of example, and simply illustrates certain example embodiments.

Referring to FIG. 1, an example operating environment 100 is illustrated in which a sensor 110 may be adjusted using an adjustment component 140 according to an embodiment. The sensor 110 of FIG. 1 includes a replaceable sub-component 120, here a replaceable sensor cap 120. A connected controller 130 may be connected to the sensor 110 via a wired or wireless connection. A wired connection may be used in an implementation where sensor 110 receives power supply from a remote source. In the example of FIG. 1, the controller 130 is illustrated as a separate component; however, an integrated controller could be employed. The controller 130 is programmed to receive and analyze measurements from the sensor. Thus, the controller contains memory, processor(s), and may also contain a display and/or network connection(s), and is configured to execute various computing functions.

Figure 3:
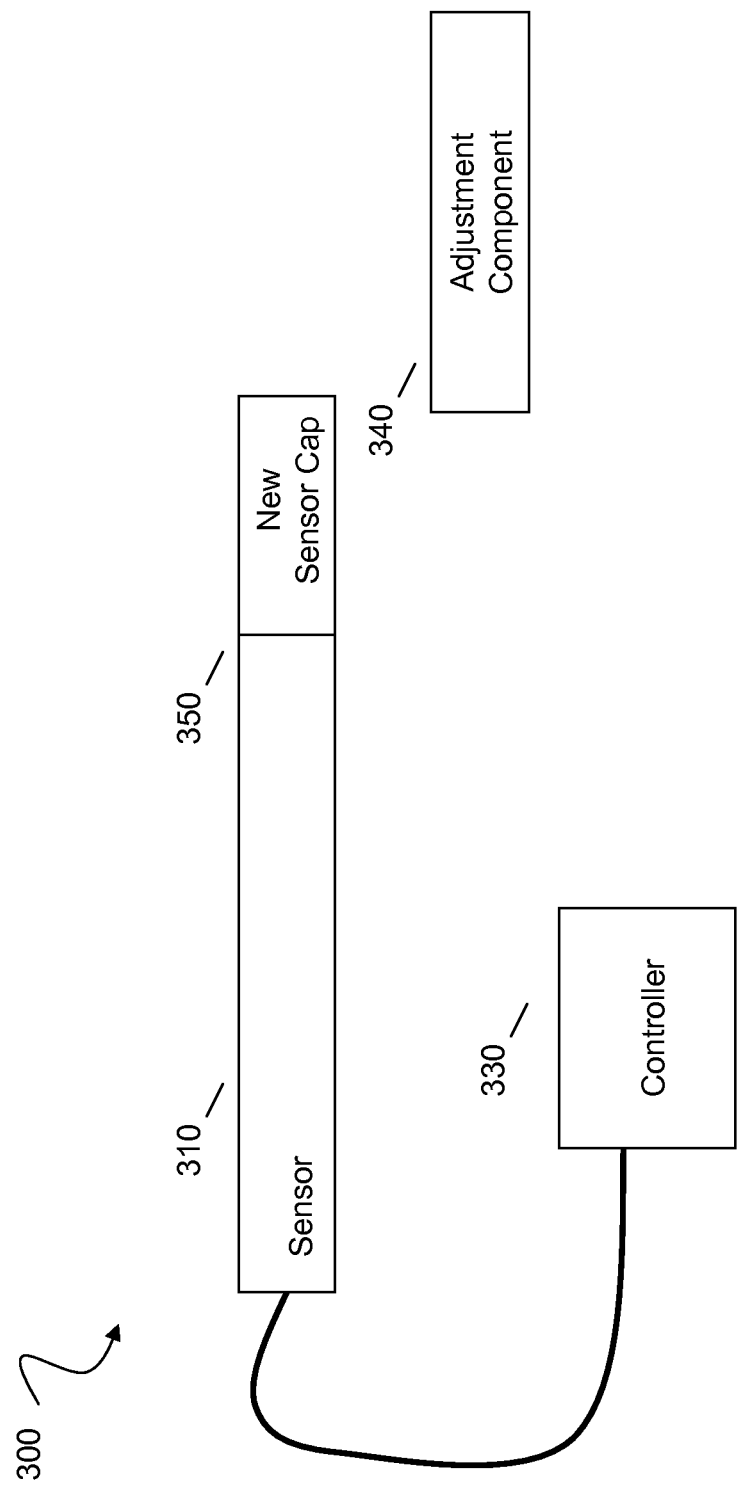
FIG. 3 illustrates an example adjustment component.

An adjustment component 140 provides the necessary adjustment information when sensor 110 is to have its sensor cap 120 replaced with another (new) sensor cap (illustrated in FIG. 3). As described herein, the new sensor cap in some conventional implementations would contain a code embodying the adjustment information, which a user would enter into the controller 130 manually. In contrast, an adjustment component 140 according to an embodiment provides for adjustment of the sensor 110 on replacement of a measurement component, such as sensor cap 120.

Figure 2:
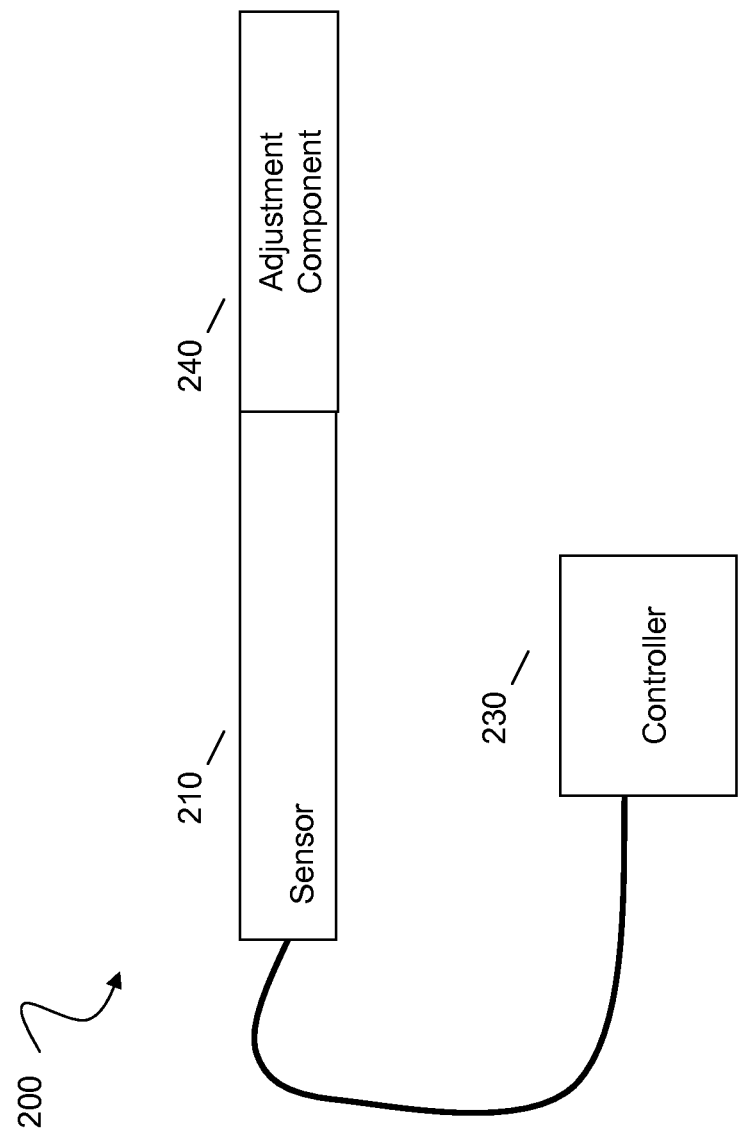
FIG. 2 illustrates an example adjustment component.

Illustrated in FIG. 2 is an example operating environment 200 in which the sensor 210 has adjustment component 240 positioned to adjust the sensor 210. The adjustment may take place automatically (for example, automatically in response to mounting adjustment component 240 on sensor 210, automatically in response to bringing adjustment component 240 into proximity of sensor 210, et cetera) or semi-automatically (for example, in response to a push of an initiation switch, or some other additional initiation).

Adjustment component 240 transmits adjustment information to the sensor 210, which may in turn transmit the adjustment information to the controller 230, although this is not necessary in some implementations. For example, sensor 210 may include memory and processor(s) such that adjustment information is stored and utilized within the sensor 210 itself without involvement of the controller 230. Thus, sensor 210 may be adjusted by adjustment component 240 to report adjusted measurements back to controller 230 or other connected device(s).

The adjustment information contains the necessary information for utilization of new sensor cap having different characteristics than a prior sensor cap (for example, sensor cap 120). The difference in characteristics again may be due in part to the sensor caps coming from different production lots. The adjustment component 240 may transmit the adjustment information to the sensor 210 while sensor contains the prior sensor cap 120, while sensor 210 has no sensor cap (that is, adjustment component may be placed over the end of the sensor 210 with no sensor cap in place), or while the sensor 210 contains a new sensor cap, so long as sensor 210 receives the adjustment information from the adjustment component 240 via a measurement channel of the sensor 210.

As illustrated in FIG. 3, an example operating environment for adjustment 300 includes sensor 310, adjusted by adjustment component 340 to use new sensor cap 350. The sensor 310 and/or the controller 330 may thus be configured with the updated adjustment information conveyed by adjustment component 350 such that use of new sensor cap 350 with the sensor 310 yields consistent measurements.

A sensor 310 may be characterized for use with a new measurement component (a sensor cap 350 in the non-limiting examples described herein) in a variety of ways. In one embodiment, a method for communicating adjustment information via a measurement channel of the sensor 310 to be adjusted is used. This allows the sensor 310 to be adjusted using the measurement channel rather than a dedicated adjustment channel, or another communication channel. Thus, for example, an optical sensor may receive adjustment information via an optical or light channel. This may be particularly appropriate in the case of sealed sensors, such as those used in aqueous environments.

Figure 4:
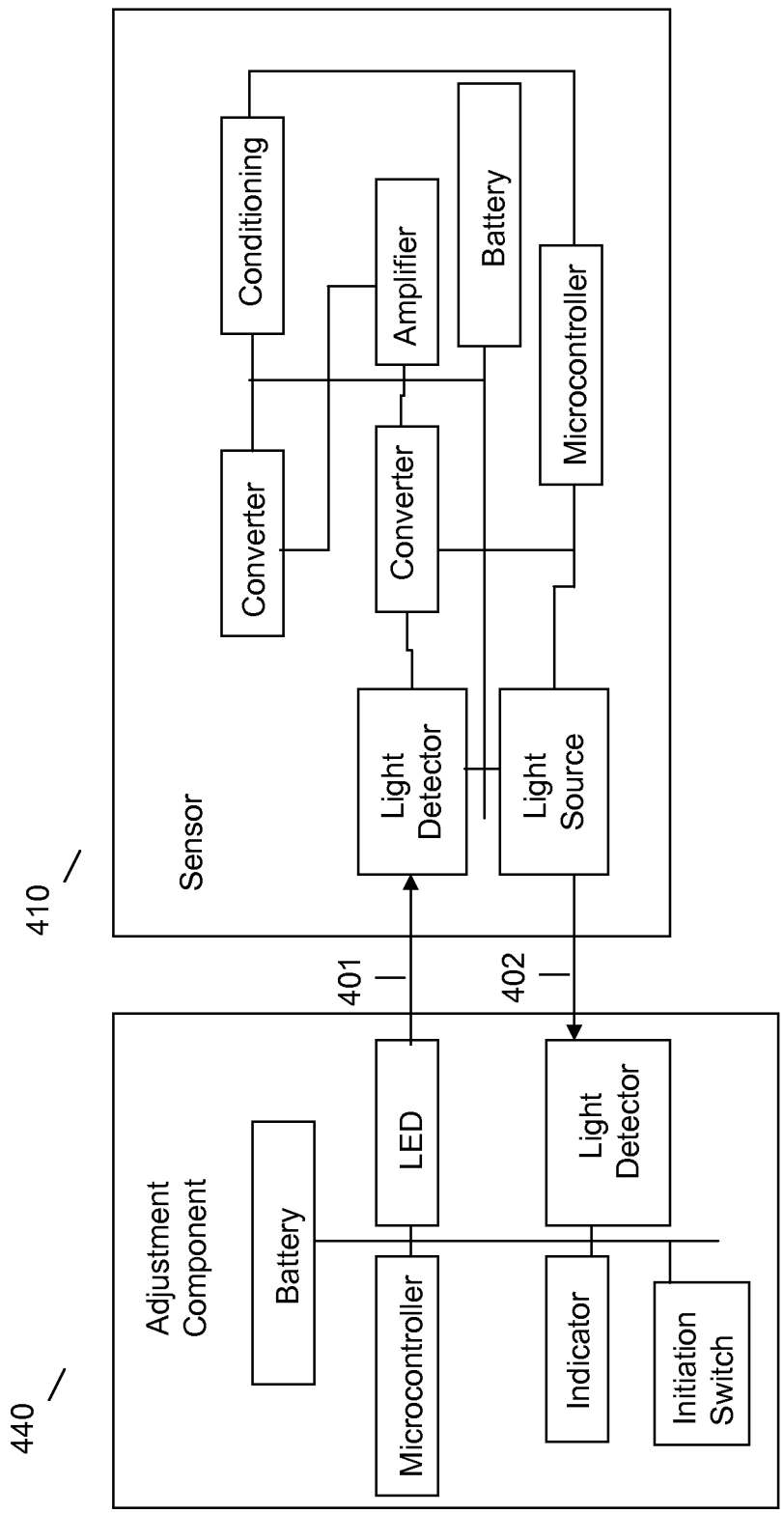
FIG. 4 illustrates an example adjustment component.

In FIG. 4 an example adjustment component 440 and example sensor 410 are illustrated. In this example, two way communications between adjustment component 440 and sensor 410 takes place; however, this is not required and a unidirectional communication from adjustment component 440 to a sensor 410 may be used. Thus, certain components/functionality may be omitted and the following is only a non-limiting example.

In the example illustrated in FIG. 4, the adjustment component 440 may include a power source (a battery in this example), a signal source (an LED light source in this example) for communicating adjustment information, a microcontroller (including one or more processors and memory) for processing information/code used to communicate adjustment information, an indicator for indicating to a user the status of an adjustment process, and a signal detector (a light detector in this example) for communicating with the sensor 410 to be adjusted. Optionally an initiation switch may also be included such that the adjustment component may be manually initiated.

For its part, the sensor 410 may include a signal detector (a light detector in this example) for its monitoring measuring function and for receiving adjustment information from adjustment component 440, a converter (light to voltage converter in this example) for converting received signals, an amplifier for amplifying received signals, another converter (analog to digital in this example) for further conversion of received signals, a signal conditioning module that appropriately conditions the signals for processing by a microcontroller (including one or more processors and memory), a communication means (a light source in this example) for communicating with the adjustment component, and a power source (a battery in this example). Additionally, the sensor 410 may also include further communication means (not illustrated) used to communicate with a controller and/or other remote device(s), for example via either a wired or wireless connection.

The adjustment component 440 transmits the adjustment information to the sensor 410 via a appropriate communication means. In the example illustrated in FIG. 4, an LED may be used to communicate 401 adjustment information to a light detector of an optical sensor 410. Thus, the measurement channel of the sensor 410 is utilized to communicate the adjustment information. The LED may transmit a predetermined light signal including an initiation signal and the adjustment information as instructed by the microcontroller of the adjustment component 440. For its part, the sensor's light detector detects the predetermined light signal, converts it appropriately (for example, to voltage), may amplify it, converts it to a digital signal, and then processes it using the sensor's microcontroller.

The sensor's microcontroller may then determine if the adjustment information has been appropriately processed (either by the sensor itself or via a connected controller), and respond appropriately. For example, if the adjustment information has been properly received and processed, sensor 410 may use its light source to so indicate to a light detector of the adjustment component 440. Otherwise, the sensor 410 could issue an error signal via its light source. For its part, the adjustment component 440 may appropriately indicate to a user if the sensor 410 has properly received and processed the adjustment information, for example via use of an indicator.

The indicator may be a light or combination of lights, an audible indicator, a graphical user interface, or some suitable combination of the foregoing. As described herein, the sensor 410 may store the adjustment information locally in memory, may locally process it to adjust the sensor's measurements, and/or may report the adjustment information back to a connected controller or other remote device for processing.

Figure 5:
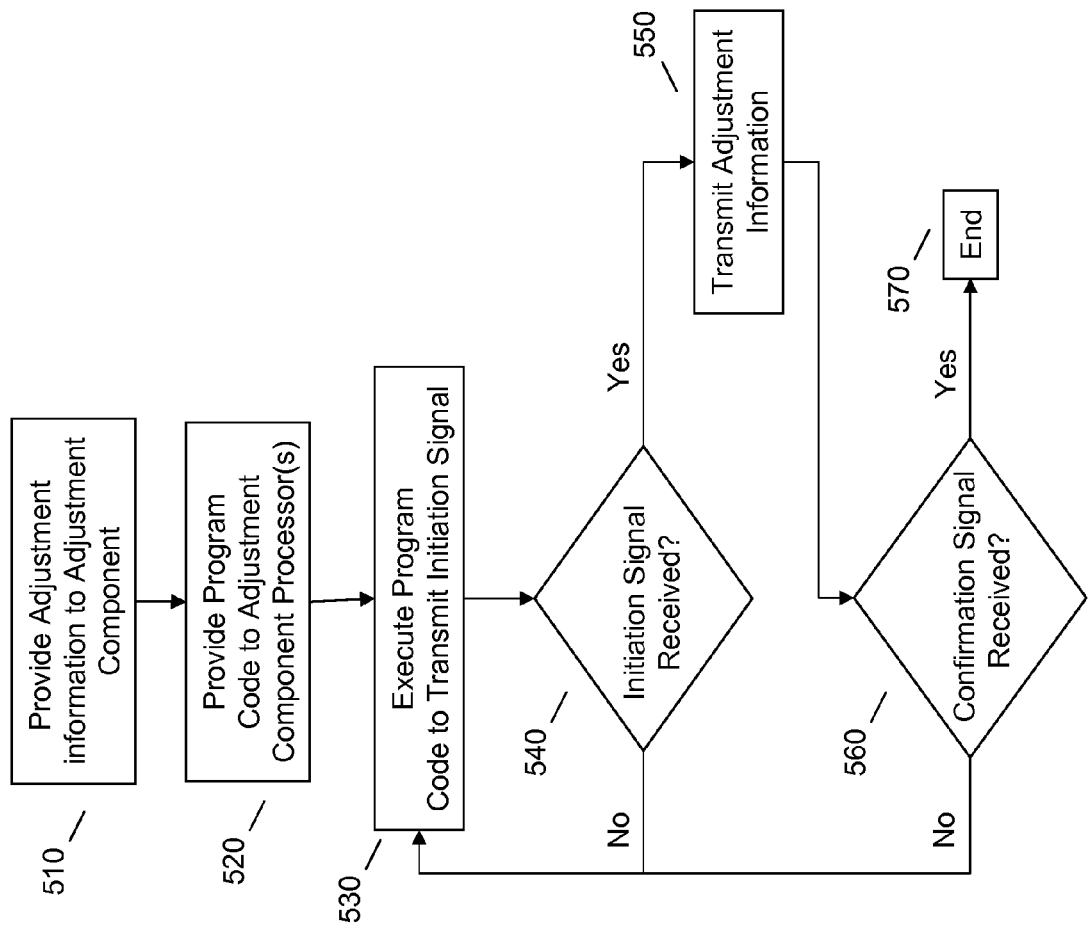
FIG. 5 illustrates an example method for adjusting a measurement system or components thereof.

In FIG. 5 an example method for adjusting a sensor is illustrated. Appropriate adjustment information is determined for the replaceable component. For example, in the case where the replaceable component is a replaceable sensor cap, a lot of sensor caps may be sampled at the point of manufacture to determine the lot's sensor cap characteristics. The appropriate normalization/standardization variables for the lot may be determined (empirically). Thus, the adjustment information may be determined ahead of time. This adjustment information may then be placed into an appropriate format and provided 510 to the adjustment component (for example, stored into memory or otherwise imparted to the adjustment component) as adjustment information. Adjustment information may be provided to an adjustment component more than once, for example for the purpose of updating a reusable adjustment component. The update may be provided in a variety of ways, such as wirelessly (for example, via an Internet or other network connection), or through a physical connection (for example, as in insertable chip or memory device, or over a physical/wired connection with another device).

The adjustment information may additionally include computer or machine readable program code instructions that allow a microcontroller of other suitable control component of the adjustment component to transmit the adjustment information to a sensor to be adjusted, as described herein. The program code is provided to the adjustment component processor(s) 520, which in turn execute the program code to transmit the adjustment information to the sensor to be characterized.

Thus, for example, the processor(s) may execute the program code 530 to transmit an initiation signal. The initiation signal's function is to signal to the sensor to be characterized that adjustment information is to be communicated. Any appropriate initiation signal may be utilized. Some non-limiting examples include a hardware initiated indication (such as a physical connection being established between the adjustment component and the sensor), a strong measurement signal (for example, a light pulse greatly in excess of a typical light pulse detected by the sensor), a patterned measurement signal (such as a predetermined initiation signal pattern), or the like.

Once the initiation signal is received 540, as for example indicated by the sensor issuing an appropriate response to the adjustment component, the adjustment component may proceed to transmit the adjustment information 550; otherwise, the process may loop back to attempt initiation again or issue an error message. Responsive to the adjustment information being transmitted, the confirmation signal may be issued by the sensor to indicate that the adjustment information has been properly received and processed. If the confirmation signal is received from the sensor 560, the process may be concluded with the sensor being appropriately adjusted for use with a new measurement component (a new sensor cap, for example); otherwise the process may loop back to attempt initiation or an error message may be issued.

Accordingly, embodiments provide for automated or semi-automated adjustment of measurement system component(s). Embodiments may utilize a measurement channel of a sensor to transmit adjustment information. Thus, even sealed sensors may be conveniently easily updated in the field.

As will be appreciated by one skilled in the art, various aspects may be embodied as a system, device, method or program product. Accordingly, aspects may take the form of an entirely hardware embodiment or an embodiment including software. Furthermore, aspects may take the form of a program product embodied in one or more device readable medium(s) having device readable program code/instructions embodied therewith.

Any combination of one or more non-signal device readable medium(s) may be utilized. The non-signal medium may be a storage medium, such as a memory included in or associated with a microcontroller of an adjustment component and/or a sensor (or a controller thereof). A storage medium may thus include, for example, an electronic, magnetic, optical, electromagnetic, infrared, or semiconductor system, apparatus, or device, or any suitable combination of the foregoing.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection, either a physical (wired connection, such as over a USB connection) or via a network, including a local area network (LAN) or a wide area network (WAN), or the connection may be made through other devices (for example, through the Internet using an Internet Service Provider).

Embodiments are described with reference to the figures. It will be understood that portions of the figures can be implemented by program instructions. These program instructions may be provided to processor(s) of a programmable data processing device to produce a machine, such that the instructions, which execute via the processor(s) of the programmable data processing device create a means for implementing the functions/acts specified.

The program instructions may also be stored in a device readable medium that can direct a programmable data processing device to function in a particular manner, such that the instructions stored in the medium produce an article of manufacture including instructions which implement the function/act specified. The program instructions may also be loaded onto a programmable data processing device to cause a series of operational steps to be performed on the programmable device to produce a process such that the instructions which execute on the programmable device provide process(es) for implementing the functions/acts specified.

The program instructions may also be loaded onto a device to cause a series of operational steps to be performed on the device to produce a device implemented process such that the instructions which execute on the device provide processes for implementing the functions/acts specified.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A system, comprising:
   a sensor adjustment component comprising:
   a memory device having adjustment information stored therein, wherein the adjustment information comprises sensor cap adjustment information that provides new optical characteristics to make a new sensor cap compatible with a sensor to operate with the new sensor cap;
   a signal source capable of producing an optical signal detectable by the sensor to be adjusted for use with the new sensor cap; and
   one or more processors;
   wherein the one or more processors operate the signal source to produce a predetermined signal pattern transmitted via an optical measurement channel to the sensor to be adjusted for use with the new sensor cap; and
   wherein the predetermined signal pattern comprises the adjustment information for adjusting the sensor to operate with the new sensor cap.

2. The system of claim 1, wherein:
   the sensor to be adjusted is an optical sensor;
   the signal source is a light engine;
   the predetermined signal pattern is a light pattern; and
   the sensor to be adjusted includes a light detector.

3. The system of claim 2, wherein the optical sensor is a luminescent dissolved oxygen optical sensor.

4. The system of claim 1, wherein the predetermined signal pattern includes an initiation signal.

5. The system of claim 4, wherein the initiation signal is a predetermined signal indicating to the sensor to be adjusted that the adjustment information is to follow.

6. The system of claim 1, wherein the adjustment information is sensor cap lot specific adjustment information.

7. The system of claim 1, wherein the sensor to be adjusted is a sealed sensor for use in an aqueous environment.

8. The system of claim 1, wherein the sensor to be adjusted is configured for use with a separate control unit.

9. The system of claim 1, wherein the sensor adjustment component is configured to be updated to allow the memory device to store new adjustment information therein.

10. The system of claim 1, further comprising:
    a sensor cap from a lot matched with the adjustment information.

11. A method comprising:
    providing adjustment information to a memory device of a sensor adjustment component, wherein the adjustment information comprises sensor cap adjustment information that provides new optical characteristics to make a new sensor cap compatible with a sensor to operate with the new sensor cap; and
    operating one or more processors to operate a signal source of the sensor adjustment component to produce a predetermined signal pattern transmitted via an optical measurement channel to the sensor to be adjusted for use with the new sensor cap;

wherein the predetermined signal pattern comprises the adjustment information for adjusting the sensor for use with the new sensor cap.

12. The method of claim 11, wherein:
the sensor to be adjusted is an optical sensor;
the sensor to be adjusted is a sealed sensor for use in an aqueous environment;
the signal source is a light engine;
the predetermined signal pattern is a light pattern; and
the sensor to be adjusted includes a light detector.

13. The method of claim 12, wherein the optical sensor is a luminescent dissolved oxygen optical sensor.

14. The method of claim 11, wherein the predetermined signal pattern includes an initiation signal.

15. The method of claim 14, wherein the initiation signal is a predetermined signal indicating to the sensor to be adjusted that the adjustment information is to follow.

16. The method of claim 11, wherein the adjustment information is sensor cap lot specific adjustment information.

17. The method of claim 11, wherein the sensor to be adjusted is a sealed sensor for use in an aqueous environment.

18. The method of claim 11, wherein the sensor to be adjusted is configured for use with a separate control unit.

19. The method of claim 11, further comprising updating the sensor adjustment component memory device to store new adjustment information therein.

20. A system, comprising:
an optical sensor adjustment component comprising:
    a memory device having a replacement component adjustment code stored therein, wherein the adjustment code comprises sensor cap adjustment information that provides new optical characteristics to make a new sensor cap compatible with an optical sensor to operate with the new sensor cap;
    a light source capable of producing a light signal detectable by the optical sensor to be adjusted for use with the new sensor cap; and
    one or more processors;
wherein the one or more processors operate the light source to produce a predetermined light pattern transmitted via an optical measurement channel to the optical sensor to be adjusted for use with the new sensor cap; and
wherein the optical sensor to be adjusted for use with the new sensor cap is a sealed sensor for use in an aqueous environment.

\* \* \* \* \*